US008658321B2

(12) United States Patent
Ratnasamy et al.

(10) Patent No.: US 8,658,321 B2
(45) Date of Patent: Feb. 25, 2014

(54) DESULFURIZATION SYSTEM AND METHOD FOR DESULFURIZING A FUEL STREAM

(71) Applicant: Sud-Chemie Inc., Louisville, KY (US)

(72) Inventors: Chandra Ratnasamy, Louisville, KY (US); Jon P. Wagner, Louisville, KY (US); R. Steve Spivey, Louisville, KY (US); Hans-Georg Anfang, Vagen (DE)

(73) Assignee: Clariant Corporation, Louisville, KY (US)

( * ) Notice: Subject to any disclaimer, the term of this patent is extended or adjusted under 35 U.S.C. 154(b) by 0 days.

(21) Appl. No.: 13/681,584

(22) Filed: Nov. 20, 2012

(65) Prior Publication Data

US 2013/0078540 A1 Mar. 28, 2013

Related U.S. Application Data

(60) Division of application No. 12/479,277, filed on Jun. 5, 2009, now Pat. No. 8,323,603, which is a continuation-in-part of application No. 11/484,224, filed on Jul. 11, 2006, now abandoned, which is a continuation-in-part of application No. 11/207,154, filed on Aug. 18, 2005, now abandoned, which is a continuation-in-part of application No. 10/932,177, filed on Sep. 1, 2004, now abandoned.

(51) Int. Cl.
*H01M 8/06* (2006.01)

(52) U.S. Cl.
USPC ........................................ 429/410

(58) Field of Classification Search
USPC ............................................. 429/410
See application file for complete search history.

(56) References Cited

U.S. PATENT DOCUMENTS

| 6,299,994 B1 * | 10/2001 | Towler et al. ............. 429/412 |
| 6,875,410 B2 * | 4/2005 | Satokawa et al. .......... 423/244.1 |
| 2004/0035055 A1 * | 2/2004 | Zhu et al. ................. 48/127.9 |
| 2006/0283780 A1 | 12/2006 | Spivey et al. |
| 2007/0196258 A1 | 8/2007 | Lee et al. |

FOREIGN PATENT DOCUMENTS

| CA | 2683630 A1 | 12/2008 |
| JP | 2003020489 A | 1/2003 |

OTHER PUBLICATIONS

International Search Report, dated Mar. 5, 2013, with respect to International Application No. PCT/US2010/037415.
Written Opinion, dated Mar. 6, 2013, with respect to International Application No. PCT/US2010/037415.

* cited by examiner

*Primary Examiner* — Randy Boyer
(74) *Attorney, Agent, or Firm* — Scott R. Cox

(57) ABSTRACT

A method for producing a substantially desulfurized a hydrocarbon fuel stream at temperatures less than 100° C. The method includes providing a nondesulfurized fuel cell hydrocarbon fuel stream that may include water and passing the fuel stream sequentially through a zeolite Y adsorbent and a selective sulfur adsorbent. The zeolite Y adsorbent may be exchanged with copper ions. The method produces a substantially desulfurized hydrocarbon fuel stream containing less than 50 ppb sulfur.

6 Claims, 1 Drawing Sheet

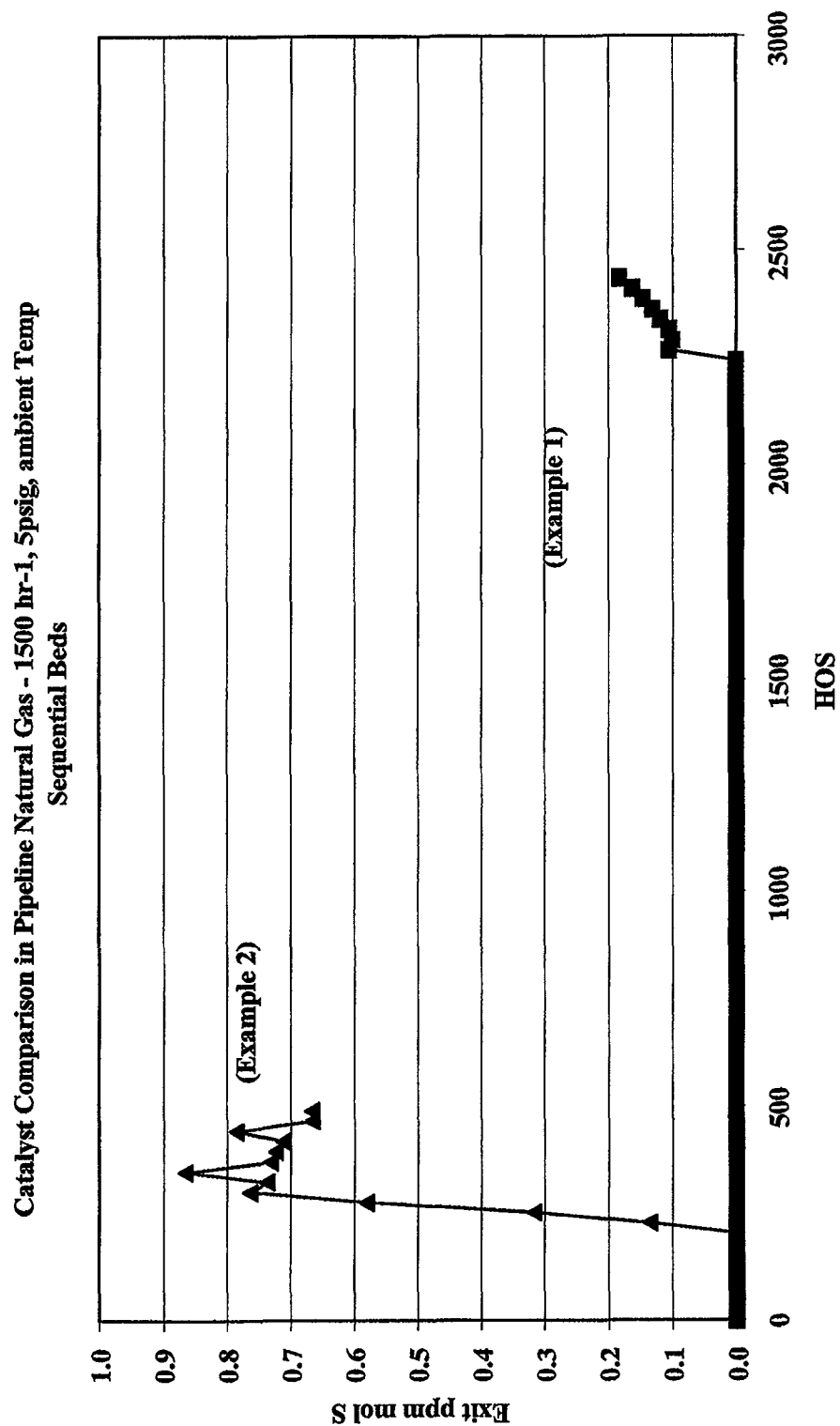

DESULFURIZATION SYSTEM AND METHOD FOR DESULFURIZING A FUEL STREAM

CROSS-REFERENCE TO RELATED APPLICATIONS

This application is a divisional application of application Ser. No. 12/479,277, filed on Jun. 5, 2009, which application is a continuation-in-part application based on application Ser. No. 11/484,224, filed on Jul. 11, 2006, now abandoned, which application is a continuation-in-part application based on application Ser. No. 11/207,154, filed on Aug. 18, 2005, now abandoned, which is a continuation-in-part application based on application Ser. No. 10/932,177, which was filed on Sep. 1, 2004, now abandoned.

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC

Not Applicable

BACKGROUND OF INVENTION (1) Field of the Invention

The present invention relates to a novel method for producing a substantially desulfurized hydrocarbon fuel stream, particularly for hydrogen generation, and more particularly for use within a fuel cell processing train, by passing a nondesulfurized hydrocarbon fuel stream, particularly natural gas, propane or liquefied petroleum gas (LPG), through a sequential sulfur adsorbent system at temperatures less than 100° C., wherein the sequential sulfur adsorbent system contains in sequence a zeolite Y sulfur adsorbent, preferably exchanged with copper ions, and at least one selective sulfur adsorbent. The present invention further relates to a process for producing hydrogen within a fuel cell processing train from a substantially desulfurized hydrocarbon fuel stream, particularly desulfurized natural gas, propane or LPG, wherein the hydrocarbon fuel stream is desulfurized using the above-described sequential sulfur adsorbent system. The present invention further includes the desulfurization system described above utilized for hydrogen generation, particularly within a fuel cell processing train, which system desulfurizes hydrocarbon fuel streams, particularly comprising natural gas, propane or LPG, at temperatures as low as ambient temperature, even if water is present in the fuel stream.

(2) Description of Related Art including information disclosed under 37 CFR 1.97 and 1.98

For hydrogen generation, particularly for use in a conventional low temperature fuel cell processing train, such as a proton exchange membrane (PEM) fuel cell, which is suitable for use in a stationary application or in a vehicle, such as an automobile, the hydrocarbon fuel stream can be derived from a number of conventional fuel sources with the preferred fuel sources including natural gas, propane and LPG. In a conventional hydrogen generation system, particularly a fuel cell processing train, the hydrocarbon fuel stream is passed over and/or through a desulfurization system to be desulfurized. The desulfurized hydrocarbon fuel stream for such fuel cell processing train then flows into a reformer wherein the fuel stream is converted into a hydrogen-rich fuel stream. From the reformer the fuel stream passes through one or more heat exchangers to a shift converter where the amount of CO in the fuel stream is reduced. From the shift converter the fuel stream again passes through various heat exchangers and then through a selective oxidizer or selective methanizer having one or more catalyst beds, after which the hydrogen rich fuel stream flows to the fuel cell stack where it is utilized to generate electricity.

Raw fuels, in gaseous or liquid phase, particularly natural gas, propane and LPG, are useful as a fuel source for hydrogen generation, particularly for fuel cell processing trains. Unfortunately, virtually all raw fuels of this type contain relatively high levels, up to as high as 1,000 ppm or so, but typically in the range of 1 ppm to 500 ppm, of various naturally occurring sulfur compounds, such as, but not limited to, carbonyl sulfide, hydrogen sulfide, thiophenes, such as tetrahydro thiophene, dimethyl sulfide, various mercaptans, including ethyl mercaptan and tertiary butyl mercaptan, disulfides, sulfoxides, other organic sulfides, higher molecular weight organic sulfur compounds, and combinations thereof. In addition, because hydrocarbon fuel streams, particularly natural gas, propane and LPG, may have different sources of origin, the quantity and composition of the sulfur compounds that may be present in the fuel streams can vary substantially. Further, these fuel stream sources may also contain water.

The presence of sulfur-containing compounds, in a hydrocarbon fuel stream can be very damaging to components of the fuel cell processing train, including the fuel cell stack itself, and such compounds must therefore be substantially removed. If not substantially removed, the sulfur compounds may shorten the life expectancy of the components of the fuel cell processing train.

An especially efficient desulfurization system is necessary for use in such fuel cell processing trains as they generally only contain a single desulfurization system. Further, desulfurization systems for such uses must have high capacity, as they may need to be in use for an extended period of time before replacement.

Several processes, conventionally termed "desulfurization," have been employed for the removal of sulfur from gas and liquid fuel streams for hydrogen generation. Adsorption of sulfur-contaminated compounds from these hydrocarbon streams using a "physical" sulfur adsorbent is the most common method for removal of sulfur compounds from such hydrocarbon fuel streams because of their relatively low capital and operational costs. (For purposes of this specification, the terms "adsorption" and "absorption" as well as "adsorbents" and "absorbents" each have the same, all inclusive meaning.) While physical adsorbents are useful, they can desorb the sulfur compounds from the adsorbent under certain operating conditions. In addition, there are often limits on the quantity of sulfur compounds which can be adsorbed by such physical sulfur adsorbents.

An additional type of adsorbent that has been useful as a desulfurization agent is a "chemical" sulfur adsorbent. However, chemical desulfurization normally requires the desulfurization system to be heated to temperatures of 150° C. to 400° C. before the nondesulfurized hydrocarbon fuel streams can be effectively desulfurized by the chemical adsorbent desulfurization system. In addition, other operational problems may occur when such chemical desulfurization processes are utilized.

While many different desulfurization processes have been suggested for hydrocarbon fuel streams, there is still a need for improved processes for desulfurization to achieve enhanced adsorption of sulfur components over an extended range of sulfur concentrations, especially at relatively low operating temperatures and pressures, and for extended periods of time. In addition, these improved processes for desulfurization must be able to achieve enhanced adsorption of sulfur compounds even when water is present in the feed stream. Further, there is a need for improved desulfurization systems to adsorb substantial quantities of a wide range of sulfur compounds, including particularly dimethyl sulfide, various mercaptans, such as ethyl mercaptan and tertiary butyl mercaptan, hydrogen sulfide, carbonyl sulfide, tetrahydro thiophene, disulfides, sulfoxides, other organic sulfides, various higher molecular weight sulfur-containing compounds and combinations thereof. Further, it is important that these improved desulfurization systems absorb this broad range of sulfur compounds effectively for an extended period of time to delay "breakthrough" of sulfur compounds as long as possible. "Breakthrough" occurs when the amount of any sulfur compound remaining in the feed stream after desulfurization is above a predetermined level. Typical "breakthrough" levels for sulfur compounds occur at less than 1 ppm. Breakthrough by virtually any of the sulfur compounds present in the hydrocarbon fuel stream is disadvantageous as substantially all sulfur compounds can cause damage to components of a hydrogen generation system, particularly for a fuel cell processing train.

In addition, some prior art adsorbents, while effective as adsorbents for some sulfur compounds, can synthesize the production of sulfur compounds even as they are removing some of the naturally occurring sulfur compounds that are present in the hydrocarbon fuel stream. (These newly produced sulfur compounds are referred to herein as "synthesized sulfur compounds.") It is important that the desulfurization system avoid the production of synthesized sulfur compounds to the greatest extent possible and for the longest period of time possible.

The foregoing description of preferred embodiments of the invention provides processes, systems and products that address some or all of the issues discussed above.

SUMMARY OF INVENTION

One of the inventions disclosed is a process for supplying a substantially desulfurized hydrocarbon fuel stream, particularly for hydrogen generation, and most particularly for use in a fuel cell processing train, comprising providing a nondesulfurized hydrocarbon fuel stream that may contain water, preparing a desulfurization system comprising a sequential sulfur adsorbent system comprising, in sequence, a zeolite Y sulfur adsorbent, preferably exchanged with copper cations, and at least one selective sulfur adsorbent, and passing the nondesulfurized hydrocarbon fuel stream through or over the desulfurization system at a temperature optimally less than about 100° C. to produce a substantially desulfurized hydrocarbon fuel stream with desulfurization levels below conventional detection limits. This level of desulfurization can be maintained for an extended period of time resulting in a surprisingly higher sulfur adsorption capacity. Preferably, this level of desulfurization is accomplished even when water is present in the fuel stream. The composition and choice of the selective sulfur adsorbent within the desulfurization system depends on the composition of the sulfur compounds which are present in that fuel stream and the extent of sulfur removal and time before breakthrough occurs that are required.

Another of the inventions is a process for generating hydrogen for use in a fuel cell processing train by use of a substantially desulfurized hydrocarbon fuel stream comprising preparing a fuel cell processing train containing the desulfurization system described above, passing a nondesulfurized hydrocarbon fuel cell fuel stream that may contain water through the desulfurization system at a temperature, preferably less than about 100° C., and introducing the substantially desulfurized hydrocarbon fuel stream to the remaining components of the fuel cell processing train.

Another of the inventions is a desulfurization system, particularly for hydrogen generation and most particularly for use in a fuel cell processing train, comprising an inlet for receiving a nondesulfurized hydrocarbon fuel stream, particularly natural gas, propane and/or LPG that may contain water, the sequential adsorbent system described above, and an outlet for passing a substantially desulfurized hydrocarbon fuel stream downstream to the remaining components of the hydrogen generation system.

A further invention is a sequential sulfur adsorbent system, particularly for hydrogen generation and most particularly for use in a fuel cell processing train, comprising, in sequence, a zeolite Y, preferably exchanged with copper cations, and one or more selective sulfur adsorbents. The choice of the specific selective sulfur adsorbent that is used within the sequential sulfur adsorbent system and the number of selective sulfur adsorbents used in the sequence depends upon the composition and quantity of the sulfur compounds that are present in the hydrocarbon fuel stream and the level of sulfur removal and time for breakthrough that are required. One preferred selective sulfur adsorbent comprises one or more manganese compounds, and copper oxide. An alternative preferred selective sulfur adsorbent comprises copper oxide and iron oxide. An additional preferred selective sulfur adsorbent comprises one or more manganese compounds, iron oxide, and copper oxide.

BRIEF DESCRIPTION OF THE SEVERAL VIEWS OF THE DRAWINGS

FIG. 1 is a graph showing a comparison of the performance of the two sequential adsorbent systems of Example 1 and Example 2 for the removal of DMS, $H_2S$, COS and TBM from a natural gas feed stream.

DETAILED DESCRIPTION OF THE INVENTION

The invention includes, but is not limited to, a method for supplying a substantially desulfurized hydrocarbon fuel stream, particularly for a hydrogen generation system and most particularly for a fuel cell processing train. Raw fuel, for use in such hydrogen generation systems, particularly a fuel cell processing train, such as natural gas, propane and LPG, must be desulfurized prior to use because such fuel streams contain relatively high levels of sulfur compounds, such as, but not limited to, thiophenes, such as tetrahydro thiophene, dimethyl sulfide, mercaptans (including ethyl, methyl, propyl and tertiary butyl mercaptan), sulfides such as hydrogen sulfide and carbonyl sulfide, various higher molecular weight organic sulfur compounds and combinations thereof. These sulfur compounds can damage components of the hydrogen generation system and the fuel cell processing train. While numerous combinations and quantities of these sulfur compounds may be present in the fuel stream, in some situations the sulfur compounds present in the fuel stream may be limited to only one or two of such sulfur compounds. Such raw fuels, particularly natural gas, generally also contain quantities of water. One feature of this invention is the ability to effectively remove a wide range of sulfur compounds from a fuel stream which contains water.

Where the raw fuel stream comprises natural gas, which is in a gaseous state at operating temperatures below 100° C., particularly below 60° C., the level of sulfur compounds, such as carbonyl sulfide, hydrogen sulfide, tetrahydro thiophene, dimethyl sulfide, mercaptans (such as ethyl, methyl, propyl and tertiary butyl mercaptan), other organic sulfur compounds, and combinations thereof may be as high as 200 ppm or so. The presence of such high levels of sulfur compounds, if not removed, results in the poisoning of components of the fuel cell processing train and may foul the fuel cell stack itself. Substantially complete removal of all of the sulfur compounds is necessary as the presence of even modest quantities of even a single sulfur compound can damage components of the fuel cell processing train.

While the desulfurization system of one embodiment of the invention can be utilized for a number of different hydrogen generation processes, one particularly preferred utilization is within a fuel cell processing train. For purposes of this specification while the use of this desulfurization system with all hydrogen generation systems is included, one preferred embodiment is the use of this system within a fuel cell processing train.

The inventors have surprisingly discovered that substantial desulfurization of a hydrocarbon fuel stream down to levels below conventional detection means can be achieved, even when water is present in the fuel stream, when a sequential sulfur adsorbent system is used for desulfurization which comprises, in sequence, a zeolite Y adsorbent, preferably exchanged with copper cations, and one or more selective sulfur adsorbents. In a preferred embodiment the sequence of use of the components in the desulfurization system is first the zeolite Y adsorbent, and then the selective sulfur adsorbent. The composition of the components of the sequential sulfur adsorbent system can be modified depending on the composition and quantity of the sulfur compounds that are present in the hydrocarbon feed stream, the extent of removal of sulfur that is required and the time that is required before breakthrough occurs.

While not a preferred embodiment, it is possible to achieve effective sulfur removal from a feed stream where two or more of the components of the desulfurization system are partially or completely blended together before placement in the desulfurization system. It is preferred, however, to separate the components from each other even though minimal blending may occur at the border between two components when those components are placed together in a desulfurization system, for example, when the components are introduced in layers without any physical separation therebetween.

The selective sulfur adsorbent(s) of the invention may be selected from a wide variety of adsorbents. As used herein a "selective sulfur adsorbent" is a material that preferentially absorbs at least one of the sulfur compounds that are commonly present in hydrocarbon fuel cell fuel streams, particularly natural gas, propane or LPG, such as hydrogen sulfide, carbonyl sulfide, tetrahydro thiophene, dimethyl sulfide, mercaptans, particularly ethyl, methyl, propyl, and tertiary butyl mercaptans, and combinations thereof, at a temperature below about 100° C., particularly below 60° C., and at pressures of about 1 bar to 18 bar.

Each selective sulfur adsorbent selectively adsorbs one or more of the sulfur compounds that are commonly present in the hydrocarbon fuel cell fuel stream, preferably natural gas. However, each of these adsorbents may be less or more effective than other of the selective sulfur adsorbents for the adsorption of particular sulfur compounds or combinations of these compounds. Further, problems can be created in the feed stream when some of the selective sulfur adsorbents are used, as these selective sulfur adsorbents can synthesize existing sulfur compounds into different, higher molecular weight sulfur compounds that are not removable from the fuel stream by the particular selective sulfur adsorbent that is utilized.

It has been surprisingly discovered that a desulfurization system can be substantially enhanced by utilizing a zeolite Y adsorbent, preferably exchanged with copper cations. In particular, the combination of one or more selective sulfur adsorbents with the copper exchanged zeolite Y adsorbent in sequence performs surprisingly better than any of the individual selective sulfur adsorbents or the copper exchanged zeolite Y, when used individually. The preferred choice and arrangement of the selective sulfur adsorbent(s) and the copper exchanged zeolite Y within the sequential sulfur adsorbent system also reduces the likelihood of the production of synthesized sulfur compounds that are sometimes created when only a single selective sulfur adsorbent is utilized in a desulfurization system.

It has been further surprisingly discovered that the removal of various combinations of sulfur compounds can be enhanced by the specific arrangement and choice of the adsorbents in the sequential sulfur adsorbent system. For the removal of various sulfur compounds, it is preferable to place the copper exchanged zeolite Y in the sequential sulfur adsorbent system prior to the selective sulfur adsorbent.

Sulfur adsorption by this system is further enhanced because some sulfur compounds, which may be synthesized to larger and more difficult to remove sulfur compounds by a particular selective sulfur adsorbent, are removed from the feed stream by the copper exchanged zeolite Y adsorbent, prior to synthesis by the selective sulfur adsorbent.

Useful selective sulfur adsorbents are selected from a group of adsorbents including, but not limited to, an adsorbent comprising substantially manganese compounds; an adsorbent which includes one or more manganese compounds and copper oxide; an adsorbent which includes one or more manganese compounds and iron oxide; an adsorbent which includes one or more manganese compounds, copper oxide and iron oxide; an adsorbent which includes zinc oxide and a carrier, particularly alumina; an adsorbent which includes activated carbon with copper oxide; an adsorbent which includes a zinc oxide/copper oxide blend, preferably containing small quantities of carbon and alumina; an adsorbent which includes copper oxide with alumina; an adsorbent which includes a copper oxide/zinc oxide blend mixed with alumina, preferably a hydrated alumina; an adsorbent which includes nickel on silica or alumina and various known selective sulfur adsorbents which include copper and zinc. Various quantities of the individual components of each of these selective sulfur adsorbents can be utilized and the quantity of the individual components can be modified to enhance the adsorption capacity of the overall desulfurization system, depending on the particular sulfur compounds that are present in the hydrocarbon fuel cell fuel stream and the quantity thereof.

A preferred selective sulfur adsorbent that can be utilized with the zeolite Y adsorbent, preferably exchanged with copper cations, in the sequential sulfur adsorbent bed system is comprised of one or more manganese compound(s) and copper oxide. The manganese compound(s) of this selective sulfur adsorbent may be utilized in any of the conventional forms previously described. The manganese compound(s) of this selective sulfur adsorbent comprise from about 25% to about 80% and preferably from about 60 to about 75% of this selective sulfur adsorbent, by weight. The copper oxide comprises from about 15 to about 40% and preferably from about 15 to about 30%, by weight, of this selective sulfur adsorbent. A binder may also be used. The binder comprises from about 5 to 20%, by weight, of this selective sulfur adsorbent. In a preferred embodiment the binder may be selected from a wide variety of clays including bentonite, diatomaceous earth, attapulgite, kaolin, sepiolite, illite and mixtures thereof. More preferably, the binder comprises bentonite clay. Promoters may also be added to this selective sulfur adsorbent to enhance its operating characteristics. This adsorbent is prepared by conventional procedures. The surface area of this manganese compound(s)/copper oxide with binder selective sulfur adsorbent ranges from about 100 to about 300 m$^2$/g, preferably from about 200 to about 300 m$^2$/g.

This manganese compound(s)/copper oxide/binder selective sulfur adsorbent when used alone has shown great utility for the adsorption of hydrogen sulfide, carbonyl sulfide, tertiary butyl mercaptan, ethyl mercaptan and mixtures thereof. In addition, this manganese compound(s)/copper oxide/binder selective sulfur adsorbent, when utilized in sequence with the copper exchanged zeolite Y adsorbent in the sequential sulfur adsorbent bed system, has shown significant adsorption for sulfur compounds contained in hydrocarbon fuel cell feed streams including, but not limited to, dimethyl sulfide, tetrahydrothiophene, mercaptans, such as methyl, ethyl, propyl, and tertiary butyl mercaptans, hydrogen sulfide, carbonyl sulfide and other sulfur compounds.

The ratio of this selective sulfur adsorbent with the copper exchanged zeolite Y adsorbent for the removal of sulfur compounds from a fuel cell fuel stream, particularly natural gas, propane and LPG, is from about 1:10 to about 10:1 and preferably from about 1:5 to about 5:1, by volume.

Other selective sulfur adsorbents, particularly of the same type, in the same quantities, and in the same sequence that may be utilized with the iron oxide/manganese compound(s), may also be utilized with this selective sulfur adsorbent and the copper exchanged zeolite Y adsorbent to form a three component system to enhance the adsorption of particular sulfur compounds that are present in a fuel cell fuel stream. The choice of the particular selective sulfur adsorbent or adsorbents used can be adjusted depending on the particular sulfur compounds that are present in the feed stream and their quantity.

An additional selective sulfur adsorbent that can be utilized with the copper exchanged zeolite Y adsorbent in a sequential adsorbent system includes one or more manganese compounds blended with iron oxide, preferably on a support, such as alumina, silica, silica-alumina, titania, and other inorganic refractory oxides. The preferred quantity of the support comprises from about 5 to about 25% by weight, preferably from about 5 to about 20% by weight, and most preferably from about 5 to about 15% by weight of the total weight of this selective sulfur adsorbent. One primary function of the support material is to provide a large and accessible surface area for deposition of the active metal compounds.

The metal compounds which are deposited on or incorporated within the support of this selective sulfur adsorbent, other than the one or more manganese compound(s), include iron oxide. In a preferred embodiment the iron oxide and manganese compound(s) together comprise at least about 60% by weight, preferably at least about 70% by weight and most preferably about 80% to about 90% of this selective sulfur adsorbent, by weight.

The ratio of the iron oxide to the manganese compound(s) by weight, should be at least about 6:1 to about 1:6 and preferably from about 1:1 to about 6:1. In a preferred embodiment the quantity of iron oxide present in this selective sulfur adsorbent exceeds the quantity of the manganese compound (s). The preferred loading of iron oxide on the support is in the range of about 40 weight percent to about 80 weight percent and, more preferably from about 50 to about 70 weight percent of the total weight of the selective sulfur adsorbent. Various forms of iron oxide may be used, such as FeO and $Fe_2O_3$ and mixtures thereof.

The one or more manganese compound(s) comprise from about 15 weight percent to about 40 weight percent, preferably from about 20 weight percent to about 40 weight percent of the total weight of the selective sulfur adsorbent. Various forms of manganese compounds can be used including $MnO_2$, $Mn_2O_3$, $Mn_3O_4$ and $Mn(OH)_4$ and mixtures thereof.

A promoter or promoters may also be added to this selective sulfur adsorbent, preferably an alkali or alkaline earth metal oxide promoter and more preferably calcium oxide, in quantities from about 5 to about 15% by weight. Alkali or other alkaline earth metal oxide promoters, such as magnesium oxide, may also, or alternatively, be utilized in combination with the calcium oxide.

The iron oxide/manganese compound(s) selective sulfur adsorbent according to the present invention may be prepared by coprecipitation, decomposition, impregnation or mechanical mixing. Preferably, this selective sulfur adsorbent is produced by coprecipitation or decomposition. The method chosen should guarantee that there has been an intensive blending of the components of the selective sulfur adsorbent.

The pore volume of the iron oxide/manganese compound (s) adsorbent produced by those procedures determined by mercury porosimetry is preferably from about 0.3 cc/g to about 0.6 cc/g. In addition, this selective sulfur adsorbent preferably has a compacted bulk density of about 0.4 to about 1.1 g/cc. Once the material is in its preliminary product form, it can be further processed to form the final selective sulfur adsorbent by pelletizing or extrusion. This selective sulfur adsorbent preferably is formed into moldings, especially in the form of spheres or pellets, preferably ranging in size from about 0.1 cm to about 1 cm in diameter. The materials for this selective sulfur adsorbent are preferably chosen to achieve a surface area of at least about 100 m$^2$/g and more preferably from about 100 m$^2$/g to about 300 m$^2$/g.

The ratio of this iron oxide/manganese compound(s) with alumina selective sulfur adsorbent to the copper exchanged zeolite Y adsorbent is from about 1:10 to about 10:1, preferably 1:5 to about 5:1, by volume. The sequence of utilization of this selective sulfur adsorbent in the sequential sulfur adsorbent bed system with the copper exchanged zeolite Y adsorbent preferably places the copper exchanged zeolite Y adsorbent prior to this selective sulfur adsorbent.

This iron oxide/manganese compound(s) selective sulfur adsorbent when used alone has shown especially good sulfur adsorption when the sulfur compounds contained in a fuel cell fuel stream comprise hydrogen sulfide, carbonyl sulfide (COS), tertiary butyl mercaptan (TBM) and ethyl mercaptan (EM). This selective sulfur adsorbent, when utilized with the copper exchanged zeolite Y adsorbent, has shown enhanced utility for adsorption of additional sulfur compounds that are commonly present in a fuel cell fuel stream including tetrahydro thiophene (THT) and dimethyl sulfide (DMS), especially when the copper exchanged zeolite Y is placed in sequence before the iron oxide/manganese adsorbent compound(s) in the sequential sulfur adsorbent bed system. However, some common hydrocarbon fuel streams do not contain these additional sulfur compounds. In this circumstance use of only the iron oxide\manganese compound(s) selective sulfur adsorbent without the copper exchanged zeolite Y adsorbent is an alternative preferred embodiment.

Other selective sulfur adsorbents can be utilized in combination with this selective sulfur adsorbent and copper exchanged zeolite Y adsorbent for the adsorption of particular sulfur compounds from a hydrogen generation system, such as a hydrocarbon fuel cell feed stream.

An additional selective sulfur adsorbent, that can be utilized with the copper exchanged zeolite Y adsorbent in the sequential adsorption system, comprises one or more manganese compounds blended with iron oxide and copper oxide, preferably on a support such as alumina, silica, silica-alumina, titania and other inorganic refractory oxide. The preferred quantity of the support comprises from about 5 to about 25% by weight. One primary function of the support material is to provide a large and accessible surface area for deposition of the active metal compound. In a preferred embodiment the manganese compounds comprise from about 10 to about 80% of the selective sulfur adsorbent with a remaining quantity including the iron oxide and the copper oxide. The preferred ratio of the iron oxide and the copper oxide can vary based on variables including the levels of sulfur compounds within the gas stream. Various forms of iron oxide may be used, such as FeO and $Fe_2O_3$ and mixtures thereof.

A promoter or promoters may also be added to this selective sulfur adsorbent, preferably an alkali or alkaline earth metal oxide promoter, such as calcium oxide, in quantities up to about 15% by weight.

The manganese compound(s)/iron oxide/copper oxide selective sulfur adsorbent according to the present invention may be prepared by coprecipitation, decomposition, impregnation or mechanical mixing. Preferably, this selective sulfur adsorbent is produced by coprecipitation or decomposition. The method chosen should guarantee that there has been an intense blending of the components of the selective sulfur adsorbent.

The pore volume of the manganese oxide/iron oxide/copper oxide adsorbent produced by these procedures determine by mercury porosimetry is preferably from about 0.1 cc/g to about 0.6 cc/g. In addition, this selective sulfur adsorbent preferably as a compacted bulk density of about 0.4 to about 1.1 g/cc. Once the material is in its preliminary product form, it can be further processed to form the final selective sulfur adsorbent by pellitizing or extrusion, preferably extrusion. This selective sulfur adsorbent preferably is formed into moldings, preferably small extrusions ranging in size from about 0.1 cm to about 1 cm in diameter. The materials for this selective sulfur adsorbent preferably chosen to achieve a surface area of at least about 100 $m^2/g$ and more preferably from about 100 $m^2/g$ to about 300 $m^2/g$. This manganese compound(s)/iron oxide/copper oxide selective sulfur adsorbent when used alone is shown especially good sulfur adsorption for hydrogen sulfide, carbonyl sulfide and mercaptans such as methyl mercaptan, ethyl, butyl and tertiary butyl mercaptans, especially when the copper exchanged zeolite Y is placed in sequence before the manganese compound(s)/iron oxide/copper oxide adsorbent compound in the sequential sulfur adsorbent system.

Other selective sulfur adsorbents can be utilized in combination with this selective sulfur adsorbent and the copper exchanged zeolite Y adsorbent for the absorption of particular sulfur compounds from a hydrogenation system, such as hydrocarbon fuel cell feed stream.

An additional selective sulfur adsorbent, that can be utilized with the copper exchanged zeolite Y adsorbent in the sequential adsorbent system, comprises copper oxide, zinc oxide and alumina, preferably a hydrated alumina. The quantity of copper oxide present is from about 15 to about 25%, the quantity of the zinc oxide is from about 5 to about 15%, and the quantity of the alumina is from about 65 to about 85%, by weight. The adsorbent is prepared by conventional procedures. The materials for this selective sulfur adsorbent are chosen so that its surface area is from about 100 to about 300 $m^2/g$, preferably from about 150 to 300 $m^2/g$. This selective sulfur adsorbent catalyst is prepared by conventional procedures.

This selective sulfur adsorbent when used alone is particularly useful for the adsorption of hydrogen sulfide, carbonyl sulfide, tertiary butyl mercaptan, ethyl mercaptan, and mixtures thereof. This selective adsorbent has shown particular utility for the adsorption of carbonyl sulfide for extended periods of time before "breakthrough" occurs, especially without the addition of any hydrolyzing agent to the feed stream.

An additional selective sulfur adsorbent that can be utilized with the copper exchanged zeolite Y adsorbent in the sequential sulfur adsorbent system in place of, or in addition to, the above described selective sulfur adsorbents comprises zinc oxide alone or in combination with a carrier. While alumina is the preferred carrier, other carriers with similar performance characteristics can be utilized. In a preferred embodiment, the zinc oxide comprises at least about 60%, preferably from about 60 to about 95%, and more preferably from about 70 to about 90%, by weight, of the selective sulfur adsorbent with the remaining portion preferably comprising alumina. Additives may be added to this selective sulfur adsorbent to enhance its capacity to absorb sulfur compounds or other performance characteristics. The surface area of this selective sulfur adsorbent ranges from 5 to about 75 $m^2/g$ and preferably from about 10 to about 50 $m^2/g$. This zinc oxide/alumina selective sulfur adsorbent is prepared by conventional procedures.

The zinc oxide alumina selective sulfur adsorbent when used alone as a sulfur adsorbent has shown good sulfur adsorption when the sulfur compounds contained within the fuel cell fuel stream comprise hydrogen sulfide and ethyl mercaptan and mixtures thereof.

Another selective sulfur adsorbent that can be utilized with the copper exchanged zeolite Y adsorbent in the sequential sulfur adsorbent system is comprised of activated carbon containing small quantities of copper oxide. In a preferred embodiment the activated carbon comprises from about 80 to about 95%, preferably 85 to 95%, by weight, of this selective sulfur adsorbent with the remaining portion comprising copper oxide. Additives may be added to the composition to enhance its performance. The activated carbon/copper oxide selective sulfur adsorbent is prepared by conventional procedures. The surface area of the composition ranges from about 300 to about 1000 $m^2/g$, with the preferred surface area being from about 500 $m^2/g$ to about 1000 $m^2/g$. This selective sulfur adsorbent is prepared by conventional procedures.

This activated carbon with copper oxide selective sulfur adsorbent when used alone has shown great utility for the adsorption of tetrahydro thiophene, tertiary butyl mercaptan, ethyl mercaptan and mixtures thereof.

Another useful selective sulfur adsorbent that can be utilized with the copper exchanged zeolite Y adsorbent in a sequential sulfur adsorbent system comprises copper oxide and zinc oxide with alumina, preferably with small quantities of carbon. In a preferred embodiment the copper oxide comprises from about 50 to about 65% and more preferably from about 50 to about 60% of the selective sulfur adsorbent, by weight. The zinc oxide comprises from about 20 to about 35% of the selective sulfur adsorbent and the alumina comprises from about 5 to about 20%, preferably from about 10 to 20% of the selective sulfur adsorbent, by weight. The quantity of the carbon, if used, should be less than 10%, preferably from about 1 to about 10%, by weight. The surface area of this selective sulfur adsorbent containing copper oxide, zinc oxide, alumina, and preferably small quantities of carbon, is from about 100 to about 300 $m^2/g$ and preferably from about 100 to about 200 $m^2/g$. The process for the preparation of this selective sulfur adsorbent is conventional.

This copper oxide/zinc oxide/alumina, preferably with small quantities of carbon, selective sulfur adsorbent when used alone is especially useful for the adsorption of hydrogen sulfide, tertiary butyl mercaptan, ethyl mercaptan, carbonyl sulfide and mixtures thereof.

An additional selective sulfur adsorbent that can be utilized with the copper exchanged zeolite Y adsorbent in the sequential sulfur adsorbent system, comprises manganese compound(s), used alone, which may be utilized in a number of forms including $MnO_2$, $Mn_2O_3$, $Mn_3O_4$ and $Mn(OH)_4$ or mixtures thereof. The surface area of the manganese compound(s) range from about 100 to about 300 $m^2/g$, and preferably from about 200 to about 300 $m^2/g$. Additional materials may be combined with the manganese compound(s) including copper, silver and magnesium to promote the performance of the manganese compound(s). Conventional methods are utilized for the formation of this selective sulfur adsorbent.

The manganese compound(s) selective sulfur adsorbent when used alone has shown great utility for the adsorption of hydrogen sulfide, tertiary butyl mercaptan, ethyl mercaptan and mixtures thereof.

An additional selective sulfur adsorbent, that can be utilized with the copper exchanged zeolite Y adsorbent in the sequential sulfur adsorbent system, comprises copper oxide with alumina, wherein the quantity of the copper oxide is from about 5 to about 25%, preferably from about 10 to about 20%, by weight, and the quantity of the alumina is from about 75 to about 95%, preferably from about 80 to about 90%, by weight. The surface area of this selective sulfur adsorbent is from about 100 to about 300 $m^2/g$ and preferably from about 150 to about 300 $m^2/g$. This selective sulfur adsorbent is prepared by conventional procedures.

This selective sulfur adsorbent when used alone has shown particularly usefulness for the adsorption of hydrogen sulfide, carbonyl sulfide, tertiary butyl mercaptan, ethyl mercaptan and mixtures thereof.

The preferred sequence of use of the adsorbents in the desulfurization system is the copper exchanged zeolite Y adsorbent placed prior to the selective sulfur adsorbent. The preferred ratio of the copper exchanged zeolite Y adsorbent to the selective sulfur adsorbent is from about 10:1 to 1:1 and preferably 5:1 to about 1:1.

The inventors have discovered that while a number of selective sulfur adsorbents may be utilized with the copper exchanged zeolite Y to remove sulfur compounds from a feed stream, the preferred selective sulfur adsorbents, particularly for hydrogen generation, and especially when water is present in the feed stream, comprise: a) one or more manganese compounds blended with copper oxide and preferably small quantities of a binder, b) one or more manganese compounds, iron oxide and preferably a support and c) one or more manganese compounds, iron oxide, and copper oxide and preferably a support.

The inventors have surprisingly discovered that while several types of zeolites may be useful as the zeolite adsorbent for this sequential sulfur adsorbent system, the preferred zeolite is a zeolite Y. Zeolite Y is substantially more hydrophobic than other zeolites, such as zeolite X. The zeolite Y may be ion exchanged with a number of different cations including, but not limited to Cu, Ag, Mn, Mg, Fe, Ca, Ce, La, Sr, Pr, and Nd. In one preferred embodiment, the ion exchanged zeolite is a copper zeolite Y.

In one embodiment of the invention, a substantial percentage of the cations of the zeolite Y are ion exchanged with copper ions using conventional ion exchange procedures, such as by treatment of the zeolite Y with copper salts, that includes, but is not limited to, copper nitrate, copper acetate and copper chloride, with copper nitrate preferred. Several methods can be used for the ion exchange procedure with ion exchange preferably occurring after the zeolite Y adsorbent has been formed into its preferred final form, such as a bead or an extrudate. The zeolite Y is ion exchanged preferably to a level of at least about 30% of its exchange capacity, more preferably at least 50%, most preferably at least 70%. The remaining ions may be sodium ions, $H^+$ and/or $NH^{4+}$ ions.

The copper exchanged zeolite Y of one embodiment of the invention generally contains some sodium ions in addition to the copper ions after the copper ion exchange. However, a portion, up to substantially all of these sodium ions, can be ion exchanged with other cations to enhance or modify the performance characteristics of the copper exchanged zeolite Y, especially for sulfur adsorption. For example, the additional cations that may be ion exchanged onto the zeolite Y to enhance its performance include zinc, cadmium, cobalt, nickel, iron, manganese, silver, gold, scandium, lithium, cerium, lanthanum, magnesium, and combinations thereof. The percentage of ion exchange of these additional metal ions can range from as little as about 1% up to about 50%, depending upon the level of copper exchange of the zeolite Y. The particular metal ions that are ion exchanged onto the copper exchanged zeolite Y depend on the particular sulfur compounds which are intended to be removed from the fuel cell fuel stream by the sequential sulfur adsorbent system of the invention.

The copper exchanged zeolite Y, when utilized as a sulfur adsorbent, has shown significant capability for the adsorption of various sulfur materials, particularly tetra hydro thiophene (THT), di-methyl sulfide (DMS), tertiary butyl mercaptan (TBM) and ethyl mercaptan (EM).

The inventors have also surprisingly discovered that an alumina component, preferably a hydrated alumina, may enhance the performance of the sequential sulfur adsorbent system. For purposes of this invention the terms "alumina hydrate" or "hydrated alumina" comprise aluminum hydroxides that commonly have the formula $Al(OH)_3$ or $AlO(OH)$. The crystalline forms of these hydrated aluminas are trihydroxides and include gibbsite, bayerite and nordstrandite. Hydrated alumina also includes aluminum oxide-hydroxides such as boehmite, pseudo-boehmite, and diaspore. The preferred forms of hydrated alumina for the alumina component of various forms of the invention include boehmite, pseudo-boehmite and gibbsite. The percentage of the alumina, which comprises hydrated alumina of the type described above, is greater than 60%, preferably greater than 80%, and most preferably, it approaches 100%.

While non-activated hydrated aluminas are the preferred form of hydrated alumina for the desulfurization system, "activated" hydrated aluminas may also have utility for some sulfur removal applications. For purposes of this invention, "activation" of a hydrated alumina requires impregnation of a hydrated alumina with one or more alkali metal or alkaline earth metal ions, preferably in an amount from about 0.01 to about 10 wt. %, wherein the wt. % is measured as a percentage weight of the impregnated alkali metal or alkaline earth metal to the total weight of the alkali metal/alkaline earth metal and aluminum in the composition. Activated hydrated alumina is generally activated by impregnation with alkali metal ions, most preferably sodium or potassium ions. Activated hydrated alumina of this type is prepared by methods recognized in the art, such as those disclosed, for example, in U.S. Pat. Nos. 3,058,800 and 4,835,338, both of which patents are incorporated herein by reference.

It has been surprisingly discovered that the capability of the selective sulfur adsorbents described above, when used individually, the hydrated alumina described above, and the copper exchanged zeolite Y, when used individually, can be enhanced dramatically by the sequential use of the copper exchanged zeolite Y and the hydrated alumina when placed prior to the selective sulfur adsorbents in the flow of the feed stream to form the sequential sulfur adsorbent system for the desulfurization of a hydrocarbon fuel cell feed stream. The use of this combination of copper exchanged zeolite Y, hydrated alumina and selective sulfur adsorbent placed in sequence, permits the adsorption of a broader range of sulfur containing compounds than has been conventionally been adsorbed using any of the components alone. For example, it has been surprisingly discovered that by the use of copper exchanged zeolite Y, hydrated alumina, and selective sulfur adsorbents placed in sequence, enhanced sulfur adsorption of a broad range of sulfur compounds, including carbonyl sulfide (COS), hydrogen sulfide ($H_2S$), tetrahydro thiophene (THT), dimethyl sulfide (DMS), and various mercaptans, including ethyl (EM), methyl, propyl, and tertiary butyl mercaptan (TBM) and combinations thereof, is possible.

The inventors have also surprisingly discovered that the sequential sulfur adsorbent system as described herein can be utilized at temperatures lower than normally utilized for conventional sulfur adsorption systems. While conventional chemical sulfur adsorbents require temperatures for the feed stream of at least about 150° C. to about 400° C., embodiments of the sequential sulfur adsorbent system can be utilized effectively to adsorb the sulfur contaminants at temperatures below 100° C. Such embodiments can be especially effective for removal of some sulfur compounds at temperatures from ambient temperature to 100° C., particularly from ambient to 60° C. Although there is no known lower limit for the ambient temperature, typically the ambient temperature at which the sulfur adsorbent systems can be used ranges between 0° C. to about 30° C.

In addition, when the sequential sulfur adsorbent system as described is used, the pressure on the feed stream can be reduced to a range from about 1 bar to about 18 bar, preferably from about 1.7 bar to about 7 bar. These pressure ranges are lower than normally are utilized for the adsorption of sulfur compounds in a conventional fuel cell processing train.

The inventors have also surprisingly discovered a method for supplying a substantially desulfurized hydrocarbon fuel stream to a fuel cell processor using the sequential sulfur adsorbent system described herein. In this process a sulfur contaminated hydrocarbon fuel stream is passed over or through the sequential sulfur adsorbent system of a fuel cell processor at a temperature from about 0° C. to about 100° C., preferably less than 60° C., and more preferably at room or ambient temperatures (20° C. to 25° C.) By passing a hydrocarbon fuel stream comprising, for example, natural gas, propane or LPG, containing sulfur components at levels up to 500 ppm, a substantial reduction in the quantity of those sulfur compounds, preferably down to a level of less than about 50 ppb, can be achieved. It has also been surprisingly discovered that this reduction in sulfur occurs even when there is water in the fuel stream up to about 1000 ppm.

The inventors have also discovered that the above-described sequential sulfur adsorbent system of the invention can be used in a desulfurizer, particularly for use in a fuel cell processing train. This desulfurizer includes an inlet for receiving the nondesulfurized hydrocarbon fuel stream, such as natural gas, propane or LPG, the sequential sulfur adsorbent system, as described herein, which is placed in a location to desulfurize the hydrocarbon fuel stream, and an outlet where the desulfurized hydrocarbon fuel stream is passed down stream for further processing. For example, the desulfurized hydrocarbon fuel stream can be passed through the fuel cell processing train to the fuel cell stack for the production of electricity.

The inventors have also surprisingly discovered that this method for supplying a substantially desulfurized hydrocarbon fuel stream is more advantageous than methods using conventional desulfurization systems as it permits desulfurization of a broader range of sulfur compounds, increases the sulfur compound breakthrough time for the system, reduces the production of synthesized sulfur compounds, reduces the required temperature of and pressure on the feed stream and permits the choice of different selective sulfur adsorbents to be used in the sequential sulfur adsorbent system depending on the sulfur compounds that are present in the particular feed stream. The compositions and methods of the processes also permit the production of a substantially desulfurized hydrocarbon fuel stream containing levels of sulfur below those achievable with conventional desulfurizing processes.

The inventors have also discovered that the sequential sulfur adsorbent system as described herein can be used in fuel cell processors for a longer period of time than conventional adsorbents and still achieve high levels of sulfur absorbency.

The inventors have also discovered that the sequential sulfur adsorbent system as described herein is also not subject to desorption of the adsorbed sulfur compounds when the conditions surrounding the sulfur adsorbent system change, as often occurs with some conventional sulfur adsorbents.

EXAMPLES

The following examples are intended to be illustrative of one embodiment of the invention and to teach one of ordinary skill in the art to make and use this embodiment. These examples are not intended to limit the invention in any way.

In order to illustrate the operation of one embodiment of the invention, the inventors have compared the performance of a first sulfur adsorbent system containing, in sequence, a copper exchanged zeolite Y followed by a selective sulfur adsorbent comprising copper oxide and manganese oxide with a second sulfur adsorbent system containing a calcium exchanged zeolite X exchanged with calcium ions and the same selective sulfur adsorbent in the same proportions. In each system the volume of the adsorbents comprised 10 ccs.

In each example, a natural gas feed stream is utilized comprising 96% methane, 2% ethane, 0.3% propane, 1% carbon dioxide, 0.5% nitrogen and 200 ppm $H_2O$. Also included in this natural gas is 0.5 ppm DMS, 2 ppm TBM, 0.2 $H_2S$, and 0.1 COS. This natural gas is passed through a reactor containing the sulfur adsorbent systems. Each zeolite adsorbent is in the form of 1/16" extrusions. The various components are loaded into the reactor and the natural gas feed stream is passed through the reactor. The temperature of the feed stream is maintained at 38° C. with a space velocity of 1500 hr$^{-1}$ at a pressure of 2 bar. "Breakthrough" for this test occurs when an amount greater than 50 ppb of sulfur is observed in the natural gas feed stream after passage through the adsorbent systems.

To determine the gas phase sulfur level of the feed stream, analysis is performed using an Agilent 6890 gas chromatograph attached to an Antek 7090 sulfur analyzer. The gas chromatograph utilizes a 60 m×320 micron DB-1 capillary column for sulfur compound separation. The Antek 7090 utilizes a sulfur chemiluminescense detector (SCD) for sulfur detection. The operational detection limit for the system is approximately 50 ppb (mole). The test unit is controlled by automation software.

Example 1

The natural gas is passed through a reactor containing, in sequence, copper exchanged zeolite Y and the selective sulfur adsorbent. The zeolite Y has a copper exchange of 58% with the remaining metal ions comprising sodium. The selective sulfur adsorbent comprises 70% by weight manganese compounds, 21% copper oxide comprising CuO and 9% silica. 80% by volume of the total adsorbent material comprises the copper exchanged zeolite Y. The DMS breakthrough of the system is shown on FIG. 1. No breakthrough occurs for H$_2$S, COS or TBM after 2444 hours.

Example 2

A further test is run wherein the zeolite comprises calcium exchanged zeolite X and the selective sulfur adsorbent of Example 1 are used in the reactor. Eighty percent (80%) of the components by volume is composed of the calcium zeolite X and 20% is composed of the selective sulfur adsorbent. When the feed stream is passed through the reactor, DMS breakthrough occurs as shown in FIG. 1. No breakthrough occurs for H$_2$S, COS or TBM after 763 hours.

As is clear from these examples, the combination of the copper exchanged zeolite Y with the selective sulfur adsorbent increases the time of sulfur breakthrough and extends the lifetime of the sequential sulfur adsorbent system over the use of calcium exchanged zeolite X with the same selective sulfur adsorbent.

As many changes and variations in the disclosed embodiments may be made without departing from the inventive concept, the invention is not intended to be limited by this description.

The invention claimed is:

1. A sulfur adsorbent system for use in removing sulfur from a hydrocarbon used in a fuel cell processing train, the sulfur adsorbent system comprising a zeolite Y adsorbent ion exchanged with a cation selected from the group consisting of Cu, Ag, Mn, Mg, Fe, Ca, Ce, La, Sr, Pr, Nd, and mixtures thereof and a selective sulfur adsorbent, wherein the sulfur adsorbent system is configured such that the hydrocarbon sequentially passes through both the zeolite Y adsorbent and then the selective sulfur adsorbent placed together in the sulfur adsorbent system at a temperature below 100° C. and wherein the desulfurization within that sulfur adsorbent system is performed substantially not by chemical desulfurization processes.

2. The sulfur adsorbent system of claim 1, wherein the zeolite Y comprises a copper exchanged zeolite Y.

3. The sulfur adsorbent system of claim 1, wherein the selective sulfur adsorbent comprise one or more manganese compounds combined with a metal compound selected from iron compounds, copper compounds, and mixture of iron and copper compounds.

4. The sulfur adsorbent system of claim 1 further comprising controlling the temperature of the feed stream while passing through the zeolite Y adsorbent and the selective sulfur adsorbent to below about 60° C.

5. The sulfur adsorbent system of claim 1, wherein the hydrocarbon feed stream further comprises water.

6. The sulfur adsorbent system of claim 1 further comprising an inlet for conveying the hydrocarbon containing sulfur to the zeolite Y adsorbent and selective sulfur adsorbent and an outlet for passing a desulfurized hydrocarbon downstream in the fuel cell processing train.

* * * * *